(12) United States Patent
Bak et al.

(10) Patent No.: US 10,285,363 B1
(45) Date of Patent: May 14, 2019

(54) AECHMEA 'PRONTOO'

(71) Applicants: Elly Bak, Rijsenhout (NL); Nicolaas David Maria Steur, Oude Niedorp (NL)

(72) Inventors: Elly Bak, Rijsenhout (NL); Nicolaas David Maria Steur, Oude Niedorp (NL)

(*) Notice: Subject to any disclaimer, the term of this patent is extended or adjusted under 35 U.S.C. 154(b) by 0 days.

(21) Appl. No.: 15/948,778

(22) Filed: Apr. 9, 2018

(51) Int. Cl.
*A01H 5/10* (2018.01)
*A01H 6/22* (2018.01)

(52) U.S. Cl.
CPC .................. *A01H 6/223* (2018.05)

(58) Field of Classification Search
CPC .................. A01H 6/223
See application file for complete search history.

(56) References Cited

U.S. PATENT DOCUMENTS

PP12,146 P2 * 10/2001 Skotak, Jr. ............... A01H 5/02
Plt./370

* cited by examiner

*Primary Examiner* — David H Kruse
(74) *Attorney, Agent, or Firm* — Cassandra Bright

(57) ABSTRACT

A new and distinct *Aechmea* hybrid named 'Prontoo' characterized by solid growth habit; funnel-form rosette plant, measuring about 50 cm in height (above pot when flowering); numerous, green color foliage (measuring about 27 to 50 cm in length and about 5 to 8 cm in width); superior floral bract production; bracts are orange white in color (closest to RHS 159D), panicle inflorescence, measuring about 10 cm in height and about 18 cm in diameter; and long-lasting habit.

5 Claims, 2 Drawing Sheets
(2 of 2 Drawing Sheet(s) Filed in Color)

AECHMEA 'PRONTOO'

FIELD OF THE INVENTION

The present invention relates to a new, distinct and stable cultivar of *Aechmea fasciata*, hereinafter referred to as 'Prontoo'. The present invention relates to seeds which are the *Aechmea* 'Prontoo', as well as, plants and plant parts produced by these seeds which have all of the morphological and physiological characteristics of the *Aechmea* 'Prontoo'. The present invention also relates to methods for producing these seeds and plants of the *Aechmea* 'Prontoo'. The present invention relates to methods for producing these seeds and plants of the *Aechmea* 'Prontoo'.

BACKGROUND OF THE INVENTION

The present invention relates to a new, distinct and stable hybrid of *Aechmea fasciata*, and hereinafter referred to by the variety denomination 'Prontoo'. The new *Aechmea* 'Prontoo' originated from a cross made in a controlled breeding program by the inventors in 2011, and then first flowered in 2013, in Assendelft, The Netherlands. The female or seed parent is the *Aechmea fasciata* inbred line identified by code 130940878 (unpatented). The male or pollen parent is the *Aechmea fasciata* inbred line identified by code 130940758 (unpatented).

*Aechmea* is a member of the Bromeliaceae family. *Aechmea* may be terrestrial or epiphytic and is native to the tropics. For the most part, species vary in diameter from 12 or 18 inches to 3 or 4 feet and have rosettes of spiny-edged leaves.

Floral bracts of *Aechmea* frequently have brilliant colors and may last for several months. The range of colors for *Aechmea* is generally from yellow through orange but may also include pink, orange, red and red-purple. Tubular, three-petaled flowers may also appear but are usually short-lived.

*Aechmea* may be advantageously grown as pot plants for greenhouse or home use. Typically, the plants are shaded from direct sunlight. During the Spring to Autumn period, the central vase-like part of the leaf rosette is normally filled with water.

*Aechmea* is native to tropical America. Leaves of *Aechmea* are usually formed as basal rosettes which are stiff and entire and in several vertical ranks. *Aechmea* plants have terminal spikes or panicles which are often bracted with petals united in a tube about as long as the calyx.

Asexual propagation of *Aechmea* is frequently performed by vegetative means through the use of tissue culture practices. Propagation of *Aechmea* can also be from off-shoots which can be detached from the mother plant and grown in an appropriate soil or bark mixture.

Methods for cultivation and crossing of *Aechmea* are well known. For a detailed discussion, reference is made to the following publications, which are incorporated herein by reference: Benzing, David H., THE BIOLOGY OF THE BROMELIADS, Mad River Press, Inc., Eureka (1980); Zimmer, Karl, BROMELIEN, Verlag, Paul Parey, Berlin (1986); and Rauh, Werner, BROMELIEN, Verlag Eugen Ulmer, Stuttgart (1981).

An *Aechmea* inbred is produced by brother/sister crossing over several generations to produce a genetically homozygous plant selection. A hybrid cultivar is produced by crossing two genetically distinct inbred lines, collecting seeds produced by the cross, and germinating seeds so-produced to make hybrid plants. The hybrid seeds and plants produced by this method are uniform with respect their morphological and physiological characteristics.

A need exists for a greater variety of *Aechmea* cultivars with attractive ornamental features. Additionally, a need exists for additional *Aechmea* hybrid cultivars that can be easily propagated by seed. The new *Aechmea fasciata* 'Prontoo' was developed through a controlled breeding program and exhibits unique, desirable and stable characteristics.

SUMMARY OF THE INVENTION

The present invention provides *Aechmea* plant selections that are solid, medium-sized, long-lasting hybrids with superior bract production and greyed white inflorescence that exhibits good keeping quality. The present invention also provides *Aechmea fasciata* plant selections with a panicle inflorescence with a unique greyed white color which distinguishes the new cultivar from typical *Aechmea fasciata*.

These and other objectives have been achieved in accordance with the present invention which provides 'Prontoo' as a new *Aechmea fasciata* cultivar that is a product of a planned breeding program conducted by the inventors, Elly Bak and Nico D.M. Steur, in Assendeift, the Netherlands, in 2011. The female or seed parent is the *Aechmea fasciata* inbred line identified by code 130940878 (unpatented). The male or pollen parent is the *Aechmea fasciata* inbred line identified by code 130940758 (unpatented).

Both parental cultivars have a sufficient degree of homozygosity such that the progeny of the cross are genetypically and phenotypically uniform. The new cultivar 'Prontoo' therefore can be produced by sexual reproduction by crossing the parental inbred lines identified by the codes 130940878 and 130940758 to produce a population of progeny plants, each of which has the combination of characteristics as herein disclosed for the new hybrid 'Prontoo'.

Seeds which are the cultivar 'Prontoo' are produced by crossing the parental inbred lines identified by the codes 130940878 and 130940758, and are deposited with the NCIMB in Aberdeen, Scotland. NCIMB accession Number 42933. 2500 seeds were deposited with the NCIMB on Apr. 3, 2018.

OBJECTS OF THE INVENTION

The present invention relates to seeds which produce *Aechmea* 'Prontoo'. The present invention also relates to *Aechmea* plants, and parts thereof, having all the physiological and morphological characteristics of *Aechmea* hybrid 'Prontoo'. The present invention relates to a plant produced from seeds which arc *Aechmea* 'Prontoo'. The present invention also relates to plant parts, such as pollen, seeds or inflorescence produced by *Aechmea* 'Prontoo'.

The present invention relates to a method of producing seed which are *Aechmea* 'Prontoo', by a crossing *Aechmea fasciata* inbred line identified by code 130940878 (unpatented) as the female or seed parent with *Aechmea fasciata* inbred line identified by code 130940758 (unpatented) as the male or pollen parent and the reciprocate cross with 130940758 (unpatented) as the male parent and harvesting seeds produced from said cross.

The present invention also relates to a method of producing plants having all the physiological and morphological characteristics of the *Aechmea* 'Prontoo' comprising the steps of (a) crossing *Aechmea fasciata* inbred identified by code 130940878 (unpatented) as a female or seed parent with *Aechmea fasciata* inbred line identified by code 130940758 (unpatented) as the male or pollen parent. (b) harvesting seeds produced from said cross; and (c) producing plants from said harvested seeds.

BRIEF DESCRIPTION OF THE PHOTOGRAPHS

The patent or application file contains at least one drawing executed in color. Copies of this patent or patent application publication with color drawings will be provided by the Office upon request and payment of the necessary fees.

The accompanying photographs illustrate the overall appearance of the new *Aechmea* cultivar 'Prontoo' showing the colors as true as is reasonably possible with colored reproductions of this type. Colors in the photographs may differ slightly from the color values cited in the detailed botanical description which accurately describes the color of 'Prontoo'.

DETAILED BOTANICAL DESCRIPTION

Figure 1:
FIG. 1 shows a side view perspective of a typical potted plant of 'Prontoo', at 14 months of age from potting size.
Figure 2:
FIG. 2 shows a close-up side view perspective of the inflorescence by a typical potted plant of 'Prontoo', at 14 months of age from potting size.

The present invention was created by the inventors, Elly Bak and Nicolaas D.M. Steur in 2011, and flowered for the first time in 2013 in Assendelft, the Netherlands.

This invention is directed to *Aechmea fasciata* plant having all the morphological and physiological characteristics of the cultivar 'Prontoo' produced from seeds which are the product of the cross of the *Aechmea fasciata* inbred line identified by code 130940878 (unpatented) as the female or seed parent with the *Aechmea fasciata* inbred line identified by code 130940758 (unpatented) as the male or pollen parent. Both parents have a sufficient degree of homozygosity such that the progeny of the cross were, and continue to be, phenotypically uniform. The new hybrid 'Prontoo' can therefore be produced by sexual reproduction by crossing of the inbred selections identified by the codes 130940878 and 130940758 to produce a population of progeny plants, each of which has the combination of characteristics herein disclosed for the new cultivar 'Prontoo'.

The new cultivar 'Prontoo' can also be produced by asexually reproducing progeny from the cross of the parental inbred lines identified by the codes 130940878 and 130940758. Asexual reproduction of the new cultivar by vegetative means by cuttings was first performed in 2014, in Assendelft, The Netherlands. The first 'Prontoo' plants propagated through the use of such cuttings flowered in 2016, in Assendelft, The Netherlands, and have demonstrated that the new cultivar reproduces true-to-type and that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be unique characteristics of 'Prontoo' which in combination distinguish this *Aechmea fasciata* as a new and distinct cultivar:
1. Stemless growth habit;
2. Funnel-form rosette plant, measuring about 50 cm in height (above pot when flowering);
3. Numerous, greyed-green color foliage (measuring about 27-50 cm in length and about 5-8 cm in width);
4. Bracts are greyed white in color (closest to RHS 159D);
5. Panicle inflorescence, measuring about 10 cm in height, when flowering and about 18 cm in diameter;
6. Long-lasting habit.

Of the many commercial cultivars known to the present inventors, the most similar in comparison to the new *Aechmea* hybrid 'Prontoo' is the *Aechmea* cultivar 'Primera'. Plants of the new hybrid 'Prontoo' differ from plants of 'Primera' primarily in color of the inflorescence.

'Prontoo' has not been tested and observed under all possible environmental conditions. The phenotype of the new cultivar may vary with variations in environment such as temperature, light intensity, frequency of fertilization, composition of fertilizer, flowering treatment, day length and humidity, without any change in the genotype of the plant.

For example, substantial differences in plant height and diameter, number of leaves, can result depending on the size of the plant at the time that flowering is induced by flowering treatment. Since treatment to induce flowering disrupts normal watering and fertilization regimens, flowering treatment of relatively smaller plants adversely affects the growth of the plant.

The aforementioned photographs, together with the following observations, measurements and values describe the new *Aechmea fasciata* 'Prontoo' as grown in a greenhouse in Assendelft, the Netherlands, under conditions which closely approximate those generally used in commercial practice. Plants of 'Prontoo' were grown in a greenhouse with day temperatures ranging from 20° C. to 28° C. and night temperatures ranging from 18° C. to 23° C. No artificial lighting or photoperiodic treatments were conducted, but plants of 'Prontoo' are forced into flowering. The following fertilizer is added when growing plants of 'Prontoo': I part nitrogen, 1 part phosphor, 3 parts Kalium. In addition, 3% of the total amount of fertilizer must be magnesium sulphate (MgSO4).

Color references are made to the Royal Horticultural Society Colour Chart (RHS), 2001 edition, except where general colors of ordinary significance are used. Color values were taken under daylight conditions in a greenhouse in Assendelft, the Netherlands. The age of the plants of 'Prontoo' described is about 12 weeks after flowering treatment.

Classification:
Botanical: *Aechmea fasciata*
Parentage:
   Female Parent: *Aechmea fasciata* inbred line identified by code 130940878 (unpatented)
   Male Parent: *Aechmea fasciata* inbred line identified by code 130940758 (unpatented)
Plant:
General Appearance and Form:
   Height: About 50 cm (including inflorescence).
   Width: About 65 cm.
   Shape: Funnel form rosette.
   Growth habit: Stemless.
   Plant Vigor: Good.
   Flowering Season: A fully grown plant can flower year-round, starting 12 weeks after induction of natural light or through flowering treatment.
   Cold Tolerance: Frost tender. Temperatures below 5° C. may damage plants.
   Fragrance: None.

Foliage:
Quantity: About 18 (depending on the size of the plant).
Size of Leaf:
   Length: About 27 cm to 50 cm (when flowering).
   Width: About 5 to 8 cm.
Overall Shape: Broadly obovate.
Apex Shape: Rounded with prickle.
Base Shape: Not narrowed.
Margin: Entire.
Texture: Soft-coriaceous.
Orientation: Leaf blades arch continuously from base.
Color: Leaf color can vary somewhat depending on growing conditions.
   Immature and Mature:
      Upper surface: Green, RHS 137A,
   with a pattern of irregular light grey bands
   and spots, closest to RHS 198D.
      Under surface: Green, RHS 137A,
         covered with layer of greyed trichomes.
      Venation: None.
Inflorescence:
Borne: Erect.
Type: Panicle.
Length: About 10 cm in height when flowering.
Diameter: About 18 cm.
Time of Bloom: A fully grown plant can produce an inflorescence containing about 70 flowers (depending on the size of the plants), and can bloom the whole year starting about 11-13 weeks after natural induction or through flowering treatment.
Duration of Bloom: Each flower blooms one (1) day and the total blooming of the whole inflorescence is about 4 weeks.
Petals:
   Number: 3 per flower.
   Length: About 3.5 cm.
   Width: About 0.7 cm.
   Overall Shape: Ligulate.
   Apex Shape: Obtuse.
   Base Shape: Fused.
Color:
   Upper and under surfaces: basal white, closest to RHS 155D. The exposed part of the petals is violet-blue, closest to RHS 92A, fading to red-purple, closest to RHS 64B.
Sepals:
   Number: 3 per flower.
   Length: About 2 cm.
   Width: About 0.8 cm.
   Overall Shape: Ligulate.
   Apex Shape: Acute.
   Base Shape: Fused.
   Color:
      Upper and under surfaces: White, closest to RHS 155D.
Bracts:
Scape Bracts:
   Quantity: About 10.
   arrangement: Sub-erect and recurving, covering the stem.
   Size:
      Length: About 8 cm.
      Width: About 2 cm.
   Overall shape: Linear-lanceolate.
   Apex shape: Acute.
   Margin: Entire.
   Color: Upper and under surfaces: orange white, closest to 159D, tip green RHS142B.
Primary Bracts:
   Arrangement: Fasciculately compound and polystichously.
   Size:
      Length: About 10 cm.
      Width: About 1.8 cm.
      Overall shape: Lanceolate.
      Apex shape: Acute.
      Base shape: Fused.
      Margin: Entire.
      Texture: Thin, coriaceous.
   Color:
      Upper and under surfaces: Orange white, closest to 159D.
Reproductive Organs:
Androecium:
Stamen:
   Number: 6 per flower.
   Length: About 2.8 cm.
   Diameter About 0.1 cm.
   Color: White with violet-blue, closest to RHS 92C.
Anther:
   Number: 6 per flower.
   Length: About 2.8 cm.
   Diameter: About 0.1 cm.
   Color: White, too small to distinguish RHS value.
Gynoecium:
Pistil:
   Number: 1 per flower.
   Length: About 3 cm.
Stigma:
   Shape: Lobed.
   Width: About 0.3 cm.
   Color: orange white, closest to 159D
Ovary:
   Position: Inferior.
   Color: White.
SEEDS/FRUIT: Seed production has not been observed.
DISEASE/PEST RESISTANCE: Neither resistance nor susceptibility to normal diseases and pets of *Aechmea* has been observed.

We claim:

1. An *Aechmea* plant named 'PRONTOO', representative seed deposited with the NCIMB in Aberdeen, Scotland. NCIMB accession Number 429332.

2. An *Aechmea* seed that produces the plant of claim 1.

3. A plant part obtained from the *Aechmea* plant of claim 1.

4. A method of producing an *Aechmea* progeny plant comprising the steps of (a) crossing *Aechmea* 'PRONTOO' produced from seed as a female or male parent with another *Aechmea* plant, and (b) selecting progeny.

5. The method according to claim 4, wherein the second *Aechmea* plant is 'PRONTOO'.

* * * * *